(12) United States Patent
Kuehnle

(10) Patent No.: US 6,498,647 B1
(45) Date of Patent: Dec. 24, 2002

(54) DEVICE FOR MEASURING VISUAL RANGE

(75) Inventor: Goetz Kuehnle, Hemmingen (DE)

(73) Assignee: Robert Bosch GmbH, Stuttgart (DE)

( * ) Notice: Subject to any disclaimer, the term of this patent is extended or adjusted under 35 U.S.C. 154(b) by 30 days.

(21) Appl. No.: 09/786,571

(22) PCT Filed: Jun. 23, 2000

(86) PCT No.: PCT/DE00/02062

§ 371 (c)(1),
(2), (4) Date: Mar. 7, 2001

(87) PCT Pub. No.: WO01/04660

PCT Pub. Date: Jan. 18, 2001

(30) Foreign Application Priority Data

Jul. 8, 1999 (DE) .......................... 199 31 825

(51) Int. Cl.$^7$ .............................. G01N 9/00; G01N 21/49
(52) U.S. Cl. ........................................ 356/437; 250/574
(58) Field of Search ................................ 356/437, 342, 356/336, 338; 250/574

(56) References Cited

U.S. PATENT DOCUMENTS 5,444,530 A * 8/1995 Wang .......................... 250/573
5,880,836 A * 3/1999 Lonnqvist ..................... 250/574

FOREIGN PATENT DOCUMENTS

| DE | 37 35 267 | 4/1989 |
|---|---|---|
| DE | 40 16 973 | 6/1991 |
| DE | 43 01 228 | 4/1994 |
| DE | 196 29 712 | 1/1998 |

* cited by examiner

Primary Examiner—Georgia Epps
Assistant Examiner—Omar Hindi
(74) Attorney, Agent, or Firm—Kenyon & Kenyon

(57) ABSTRACT

A device, by which an unadulterated visibility range can be determined that is independent of the scattering-medium characteristics, determines according to the LIDAR principle the instantaneous visibility range from backscatter light reflected in the scattering medium in front of a vehicle. An evaluation unit is also provided which normalizes a plurality of backscatter measuring curves recorded in succession over time. It forms an average measuring curve from the normalized measuring curves, and derives from at least one measured value of the averaged measuring curve, a visibility range which is independent of the backscattering characteristics of the scattering medium. Using this visibility range thus ascertained, an adaptive compensation of the instantaneously ascertained visibility range is carried out in the evaluation unit.

5 Claims, 2 Drawing Sheets

DEVICE FOR MEASURING VISUAL RANGE

FIELD OF THE INVENTION

The present invention relates to a device for measuring visibility range, particularly for motor vehicles, which has at least one optical transmitting element, at least one optical receiving element and a measuring-signal evaluation unit which ascertains an instantaneous visibility range from the light reflected from one or more space zones which are at different distances.

BACKGROUND INFORMATION

Such a device is known from German Patent No. DE 196 29 712 This known device measures backscattering according to the LIDAR principle. In this case, a light transmitter (e.g. a laser or a photodiode) emits light pulses into the surroundings located in front of a vehicle. Depending on the scattering medium (e.g., fog, snow, rain, smoke, etc.) in the surroundings in front of the vehicle, a greater or lesser portion of the light is reflected after the interaction with the scattering medium, and received by one or more receiving elements (e.g. photodiode). The visibility range is ascertained from the relationship of emitted light to reflected light. However, there are several interference effects on the transmission path of the light which influence the received signals, and thus invalidate the visibility-range measuring result. Sources of error when measuring the visibility range are, for example, a change in the transmitting power of the emitted light because of temperature changes or aging of the transmitting element, for instance, or soiling of the optical system pre-connected to the transmitting and receiving elements, or soiling of the motor-vehicle windshield through which the emitted and received light pulses pass. To eliminate these interference effects, according to the related art mentioned, the backscatter light is determined from two space zones which are at different distances. The indicated interference effects can be eliminated by forming the ratio of the received signals.

It turns out that the measuring signals received by the optical receiver are very strongly dependent on the backscattering properties, i.e. on the type of scattering medium. For example, in the case of fog, the backscatter characteristics are dependent on the droplet-size distribution. However, an unadulterated visibility-range measurement is only possible when the type of scattering medium has no influence on the visibility-range measurement. Therefore, an object of the present invention is to provide a device of the type indicated at the outset which permits a visibility-range measurement that is independent of the type of scattering medium.

SUMMARY OF THE INVENTION

The indicated objective is achieved, in that means are provided which normalize a plurality of successively recorded measuring curves, each of which is composed of a plurality of measured values of light reflected from space zones at different distances. The means form an average measuring curve from the normalized measuring curves, and derive from at least one measured value of the averaged measuring curve, a visibility range which an evaluation unit uses for the adaptive compensation (adjustment) of an instantaneously ascertained visibility range. The instantaneous visibility range is determined according to the related art from the light reflected from one or more space zones that are at different distances.

The instantaneous visibility range is measured without great time delay, and can be implemented repeatedly within a second. The instantaneous visibility range is compensated according to the present invention using a measured visibility range resulting from a longer-lasting averaging process of past measured values, with the goal of eliminating the influence of the scattering-medium characteristics on it. The averaging process for determining the visibility range used as compensation makes it superfluous to send out light signals having very high levels which represent a danger for the eyes. The ascertainment of the visibility range that is independent of the scattering medium, which is more tedious because of the averaging process, does not delay the actual measurement of an unadulterated visibility range, since it is merely used as a compensation variable for the instantaneous visibility range that is determined very quickly, but not without influence by the type of scattering medium.

Accordingly, it is expedient that the means normalize all measuring curves, recorded in succession over time, to the maximum value of the measuring curves.

A classifier, operating according to the fuzzy principle, advantageously divides the respectively ascertained, compensated visibility ranges into distance classes.

The means advantageously set a plurality of measured values from the averaged measuring curve in relation to one another, and derive the visibility range therefrom.

Additional means can be provided which acquire from the visibility range, which has been derived from the averaged measuring curve, information about the type of medium impairing the visibility range.

BRIEF DESCRIPTION OF THE DRAWING

The present invention shall now be explained in greater detail.

DESCRIPTION OF AN EXEMPLARY EMBODIMENT

Figure 1:
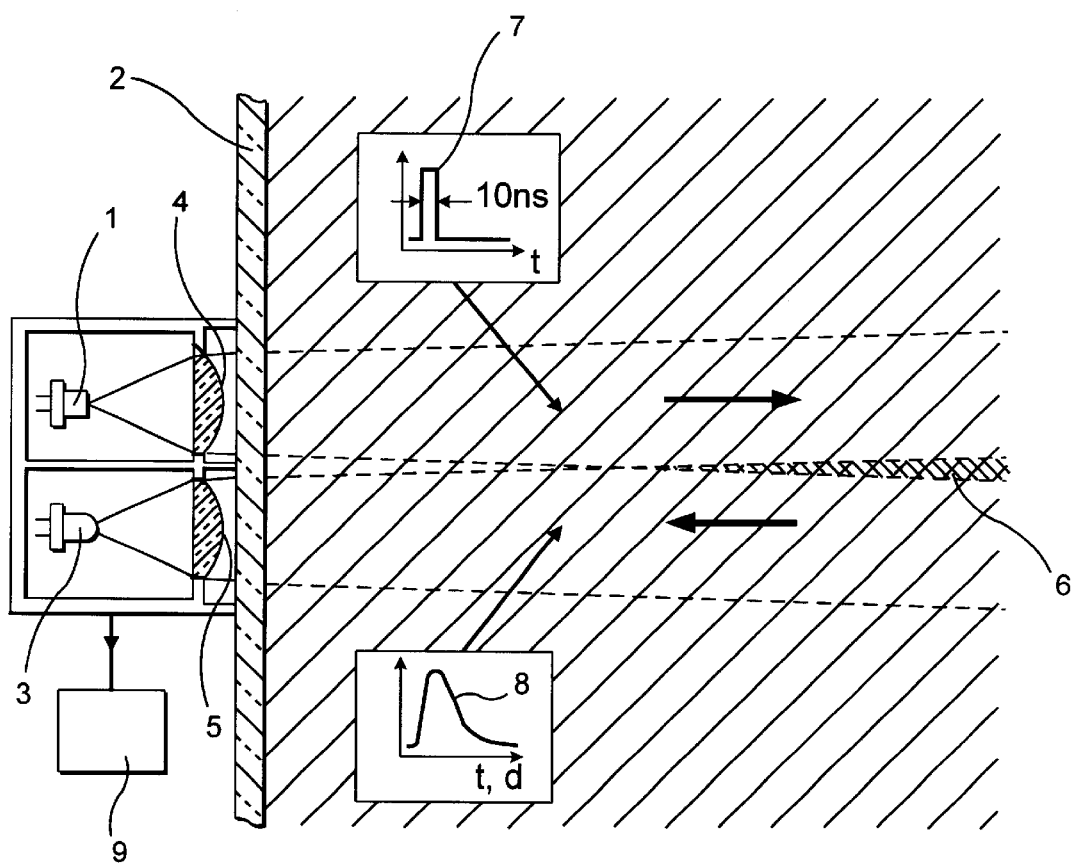

FIG. 1 shows a device for measuring visibility range.

Figure 2A:
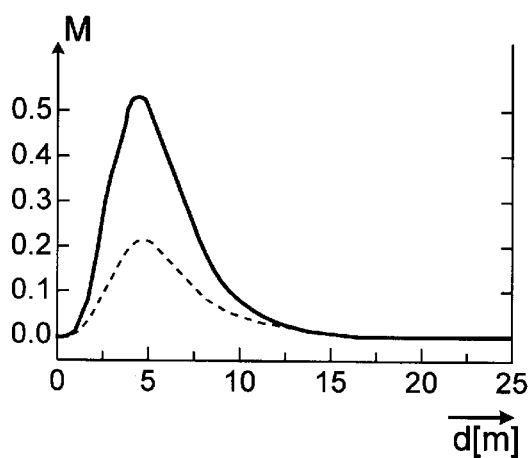

FIG. 2a shows two measuring curves.

Figure 2B:
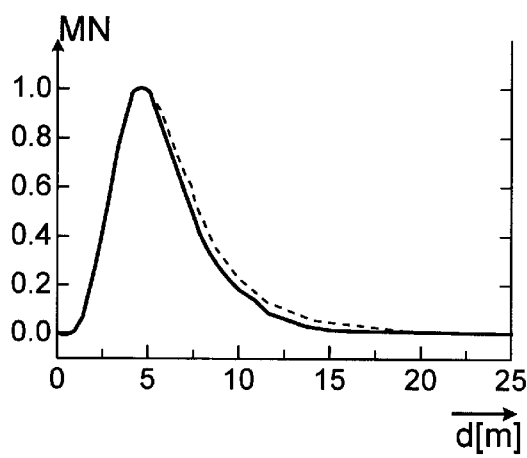

FIG. 2b shows two further measuring curves.

Figure 3:
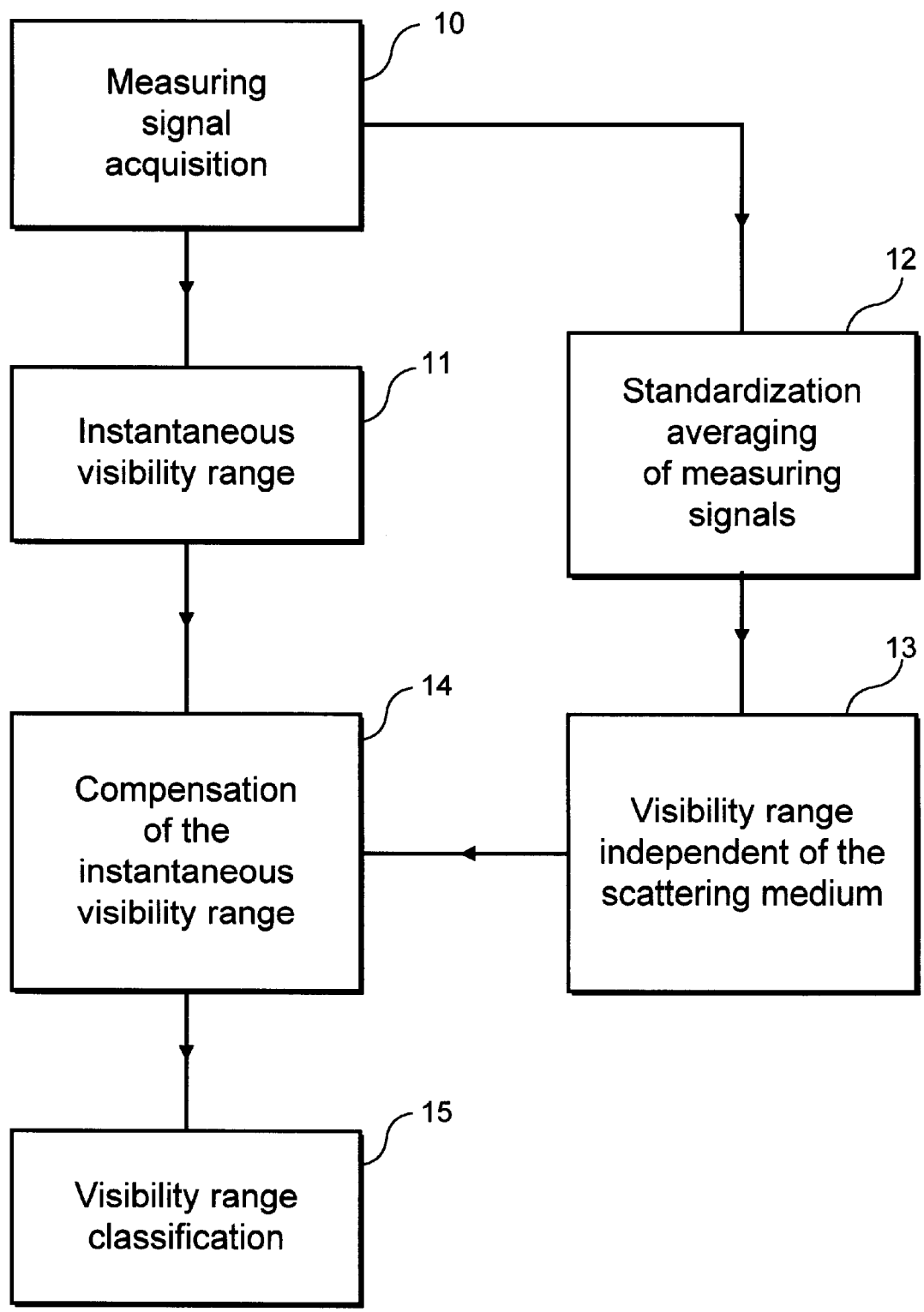

FIG. 3 shows a flowchart for ascertaining the visibility range.

DETAILED DESCRIPTION

FIG. 1 shows an arrangement intended to be used for measuring the visibility range in the region in front of a vehicle. The arrangement functions according to the known LIDAR (light detecting and ranging) principle. It possesses a transmitting element 1 (e.g. an IR laser diode) which radiates light pulses from the interior of the vehicle through windshield 2 into the region in front of the vehicle, and at least one optical receiving element 3 (e.g. PIN diode) which receives the light, backscattered from the scattering medium (e.g. rain, fog, snow, smoke, etc.) located in front of the vehicle, and converts it into an electrical signal. Arranged in front of optical transmitting element 1 and in front of optical receiving element 3 are focusing lenses 4 and 5, respectively, to restrict the emitted light to a spatially bounded light beam on the one hand, and on the other hand, to focus the backscattered light onto receiving element 3. The spatial bounding of the two light beams denoted by arrows is indicated in FIG. 1 by broken lines.

The optical axes of transmitting element 1 and of receiving element 3 are aligned with respect to one another in such a way that the transmitting beam and the receiving beam form an overlapping region 6 which is cross-hatched in FIG. 1. Thus, receiving element 3 captures the part of the emitted light which is backscattered from the scattering medium, indicated in FIG. 1 by a diagonal hatching, in overlapping region 6. As marked in FIG. 1, transmitting element 1 emits a short light pulse 7 of approximately 10 ns duration. The time characteristic 8 of the component backscattered from emitted light pulse 7 is likewise shown in FIG. 1. The time dependence of the amplitude of the backscatter light received by receiving element 3 is in a direct relationship to the distance of the space zone from which the backscattered light comes. That is to say, the further the space zone is from receiving element 3, the smaller is the backscattered component of transmitting light pulse 7, and the shorter the distance of the space zone is to receiving element 7, the higher is the portion of emitted light pulse 7 backscattered from this space zone. Instead of recording a backscatter-light profile 8 as a function of the distance of space zones which are at different distances using a single optical receiving element 3 as is shown in FIG. 1, backscatter light from variably set-apart space zones can also be received using a plurality of receiving elements, as described in the German Patent DE No. 196 29 712. In this case, the optical axes of the receiving elements have different angles with respect to the optical axis of the transmitting element.

Connected to receiving element 3 is an evaluation unit 9 which determines the visibility range in the region in front of the vehicle from the output signal of receiving element 3 receiving the backscattered light.

The flowchart shown in FIG. 3 clarifies the ascertainment of the visibility range from the output signal of optical receiving element 3. In a first step 10, measuring signals are acquired, i.e., the output signal of receiving element 3 is sampled in a time-discrete manner. Each sampling value then represents the amplitude of the backscattered light from a specific space zone.

In the next step 11, the instantaneous visibility range is ascertained from one or more of the measured values derived from the sampling. In the simplest case, the visibility range can be determined from a single measured value which represents the amplitude of the backscattered light from one space zone having a defined distance to receiving element 3, because the amplitude of the indicated measured value is generally proportional to the light attenuation through the scattering medium, from which the visibility range can be calculated. The instantaneous visibility range can also be determined by setting a plurality of measured values in relation to one another. Expressed therein is the light-attenuating effect of the scattering medium between space zones at different distances, and there exists in this a direct connection to the visibility range. Through the ratio formation of a plurality of measured values, interference effects such as changes in the transmission power due to temperature fluctuations, soiling of focusing optics 4, 5, soiling of windshield 2, etc. can be eliminated.

Provided that it is a homogenous scattering medium, the instantaneous visibility range ascertained in the indicated manner is correct. As a rule, however, the scattering medium does not have a homogenous characteristic; fog, for example, has quite a variable droplet-size distribution. It turns out that the amplitude of the measuring signal is very strongly dependent on the characteristic of the scattering medium. If, as in method step 11, one thus depends on the measured values from the measuring signal received by optical element 3 when determining the instantaneous visibility range, then the result of the determination of the instantaneous visibility range is false. To nevertheless obtain a correctly measured visibility range, in method step 14, the visibility range, which in method step 11 is instantaneously ascertained repeatedly in a second, is corrected. Specifically, the correction is made through an adaptive compensation of the instantaneous visibility range by a visibility range that is independent of the scatter-medium characteristics and is determined in method steps 12 and 13.

FIG. 2a shows two measuring curves of the backscattered light, where in both cases, let us say, the same visibility range was present, but because of the different properties of the scattering medium, one time a strong backscattering (solid line of the measuring curve) was present, and another time a weak backscattering (measuring curve indicated by broken line) was present. From this it becomes clear that an unaltered evaluation of measured values from a measuring signal cannot result in a correct visibility range.

To eliminate the dependence of the amplitude of measuring signal M on the characteristic of the scattering medium, in method step 12, a plurality of successively recorded measuring curves are normalized (scaled), and subsequently all the normalized measuring curves are averaged. For example, in FIG. 2b, two measuring curves, which have been recorded in the case of a scattering medium with different visibility ranges but identical backscattering characteristics, have been normalized to the maximum value of the measuring curve with the solid line. Incidentally, all measuring curves can also be normalized to a different uniform value. A comparison of the two normalized measuring curves MN shows that the different light attenuation, i.e. the different visibility range, results in only a very small change in the measuring-signal profile. Such a small change in a measuring curve, which a visibility-range measuring result that is independent of the scattering-medium characteristic would bring, is, however, lost in the signal noise. This could be counteracted by emitting light pulses with a correspondingly higher power. However, to protect the eyes, the signal power must not exceed a specific power level. A measuring result of the light attenuation in the scattering medium which is scarcely impaired by noise can also be achieved with a lower power of the emitted light, in that a plurality of measuring signals are received, normalized, and subsequently an averaged measuring curve is formed therefrom.

In method step 13, a visibility range which is independent of the scattering-medium characteristics is now attained by setting a plurality of sampling values from the averaged measuring signal, for example, in relation to one another. Given two different intervals d from measured values x1, x2 extracted from the normalized, averaged measuring signal, the visibility range that is independent of the scattering-medium characteristics could be derived from variable y which is formed in the following manner:

$$y = \frac{x1}{x2} \quad \text{or} \quad y = \frac{x1}{x1 + x2} \quad \text{or} \quad y = \frac{x1}{\sqrt{x1^2 + x2^2}}$$

or $$y = \lg(x1) - \lg(x2)$$

In method step 14, the instantaneous visibility range, which is very quickly determinable without a time-consuming averaging process, is adaptively adjusted to the visibility range that is independent of the scattering-medium characteristics and is yielded from past measuring signals by a normalization and averaging process. Thus, without great time delay, it is possible to determine an instantaneous visibility range that is largely unadulterated by scattering-medium characteristics and further unknown backscattering properties (e.g., by focusing optics 4, 5 and windshield 2) and other influences, for example, because of a transmitting-power change, the sensitivity of the receiving elements, etc.

When working with the process for determining the visibility range, independent of the scattering-medium characteristics, from an averaged measuring curve, it is possible to derive further information, for example, about the type of medium (radiation fog, advection fog, rain, snow, smoke, etc) adversely affecting the visibility range. The relationship of backscattering intensity (measuring-signal amplitude) and light attenuation, from which the visibility range is yielded, is different for different scattering media, so that it is possible to draw conclusions about the type of scattering medium from the indicated relationship.

FIG. 3 shows yet a further method step 15, according to which the respective ascertained visibility range is classified, for example, according to a fuzzy algorithm. That is to say, the respective ascertained visibility range is assigned to one of a plurality of visibility-range classes. For example, a visibility-range class distribution could be: less than 50 m, between 50 and 100 m, between 100 and 150 m, etc.

For example, the measured visibility range can be displayed to the driver; it can also be used to intervene in an automatic cruise-control and proximity-control system, or to control the lighting system in adaptation to the visibility range.

What is claimed is:

1. A device for measuring a visibility range for a motor vehicle, comprising:

at least one optical transmitting element;

at least one optical receiving element;

an arrangement for normalizing a plurality of successively recorded measuring curves, each of the measuring curves being composed of a plurality of measured values of light reflected from variably distant space zones, the arrangement forming an average measuring curve from the normalized measuring curves and deriving a visibility range from at least one measured value of the averaged measuring curve; and a measuring-signal evaluation unit for ascertaining an instantaneous visibility range from light reflected from at least one of a plurality of space zones that are at various distances, the evaluation unit performing an adaptive compensation of the ascertained instantaneous visibility range using the derived visibility range.

2. The device according to claim 1, wherein the arrangement normalizes all of the measuring curves, recorded in succession over time, to a maximum value of the measuring curves.

3. The device according to claim 1, further comprising a classifier operating according to the fuzzy principle, the classifier dividing respectively ascertained, compensated visibility ranges into distance classes.

4. The device according to claim 1, wherein the arrangement sets a plurality of measured values from the averaged measuring curve in relation to one another, the arrangement deriving the visibility range as a function of the measured values.

5. The device according to claim 1, further comprising means for gaining information form the derived visibility range about a type of medium adversely affecting the visibility range.

* * * * *